United States Patent
Lee et al.

(10) Patent No.: US 10,744,022 B2
(45) Date of Patent: Aug. 18, 2020

(54) FORCE TRANSMITTING FRAME AND MOTION ASSISTANCE APPARATUS INCLUDING THE SAME

(71) Applicants: Samsung Electronics Co., Ltd., Suwon-si, Gyeonggi-do (KR); Korea University of Technology and Education Industry-University Cooperation Foundation, Cheonan-si, Chungcheongnam-do (KR)

(72) Inventors: Youn Baek Lee, Yongin-si (KR); Jung-Yun Choi, Seoul (KR); Yong Jae Kim, Cheonan-si (KR)

(73) Assignees: SAMSUNG ELECTRONICS CO., LTD., Gyeonggi-Do (KR); KOREA UNIVERSITY OF TECHNOLOGY AND EDUCATION INDUSTRY-UNIVERSITY COOPERATION FOUNDATION, Chungcheongnam-Do (KR)

(*) Notice: Subject to any disclaimer, the term of this patent is extended or adjusted under 35 U.S.C. 154(b) by 202 days.

(21) Appl. No.: 15/607,909

(22) Filed: May 30, 2017

(65) Prior Publication Data
US 2018/0104083 A1    Apr. 19, 2018

(30) Foreign Application Priority Data
Oct. 18, 2016    (KR) .................. 10-2016-0135106

(51) Int. Cl.
*A61F 5/01*    (2006.01)
*A61F 2/60*    (2006.01)

(52) U.S. Cl.
CPC ............. *A61F 5/0127* (2013.01); *A61F 2/60* (2013.01); *A61F 5/0111* (2013.01); *A61F 5/0102* (2013.01)

(58) Field of Classification Search
CPC ........ A61F 5/0127; A61F 5/0111; A61F 2/60; A61F 5/0102; A61F 2005/0137; A61F 2005/0141; A61F 2005/0144; A61F 2005/0146; A61F 2002/6614; A61F 2002/6621; A61F 2002/6642; A61F 2/66;
(Continued)

(56) References Cited

U.S. PATENT DOCUMENTS 6,443,993 B1    9/2002    Koniuk
8,287,477 B1    10/2012   Herr et al.
(Continued)

FOREIGN PATENT DOCUMENTS

EP    2 997 952 A1    3/2016
JP    H09-103443 A    4/1997
(Continued)

OTHER PUBLICATIONS

Extended European Search Report dated Apr. 5, 2018 for EP Application No. 17186777.3.
(Continued)

*Primary Examiner* — Brian A Dukert
*Assistant Examiner* — Rebecca Lynee Zimmerman

(57) ABSTRACT

A force transmitting frame including a base, a first longitudinal member connected to the base, a second longitudinal member configured to slide with respect to the base, and a first fastener configured to fasten one end of the first longitudinal member and one end of the second longitudinal member is provided.

22 Claims, 23 Drawing Sheets

(58) Field of Classification Search
CPC .............. A61F 2005/0148; A61H 1/02; A61H 2201/165; A61H 1/0266; A61H 2201/164; A61H 3/04; A61H 2003/007; A61B 1/005; G05B 2219/40305; B25J 9/006
See application file for complete search history.

(56) References Cited

U.S. PATENT DOCUMENTS

| | | |
|---|---|---|
| 8,545,424 B2 | 10/2013 | Hirata et al. |
| 9,084,689 B2 | 7/2015 | Herr |
| 2008/0313935 A1 | 12/2008 | Trifunovic |
| 2013/0046218 A1 | 2/2013 | Wiggin et al. |
| 2014/0000125 A1* | 1/2014 | Butler .................. A43B 13/386 36/43 |
| 2014/0074293 A1* | 3/2014 | Orita ...................... G05B 13/00 700/261 |
| 2015/0182366 A1 | 7/2015 | Takenaka et al. |
| 2016/0081870 A1 | 3/2016 | Lee et al. |

FOREIGN PATENT DOCUMENTS

| | | |
|---|---|---|
| JP | 2006-500151 A | 1/2006 |
| JP | 2010-512819 A | 4/2010 |
| JP | 5013881 B2 | 8/2012 |
| JP | 2013/233421 A | 11/2013 |
| KR | 10-2000-0047310 | 7/2000 |
| KR | 10-2010-0089013 | 8/2010 |

OTHER PUBLICATIONS

Collins, Steven H. et al., "Reducing the energy cost of human walking using an unpowered exoskeleton," Nature, Jun. 11, 2015, 522 (7555): 212-215, doi:10.1038/nature14288.

Mooney, Luke M. et al., "Autonomous exoskeleton reduces metabolic cost of human walking", Journal of NeuroEngineering and Rehabilitation 2014, 11:151.

Malcolm, Philippe et al., "A Simple Exoskeleton That Assists Plantarflexion Can Reduce the Metabolic Cost of Human Walking", PLOS ONE, Feb. 2013, vol. 8, Issue 2.

* cited by examiner

1

3

9

FORCE TRANSMITTING FRAME AND MOTION ASSISTANCE APPARATUS INCLUDING THE SAME

CROSS-REFERENCE TO RELATED APPLICATION

This application claims under 35 U.S.C. § 119 to Korean Patent Application No. 10-2016-0135106, filed on Oct. 18, 2016, in the Korean Intellectual Property Office, the entire contents of which are incorporated herein by reference in their entirety.

BACKGROUND

1. Field

At least one example embodiment relates to a force transmitting frame and/or a motion assistance apparatus including the same.

2. Description of the Related Art

Motion assistance apparatuses enabling the elderly and/or patients having joint problems to walk with less effort, and motion assistance apparatuses increasing muscular strength of users for military purposes are being developed.

SUMMARY

Some example embodiments relate to a force transmitting frame.

In some example embodiment, the force transmitting frame may include a base; a first longitudinal member connected to the base; a second longitudinal member configured to slide with respect to the base; and a first fastener configured to fasten a first end of the first longitudinal member to a first end of the second longitudinal member.

In some example embodiment, a middle region of the first longitudinal member and a middle region of the second longitudinal member are configured to move relative to each other.

In some example embodiment, a middle region of each of the first longitudinal member and the second longitudinal member is flexible with respect to a force applied in a direction perpendicular to a longitudinal direction thereof.

In some example embodiment, the force transmitting frame is shaped such that a distance between the first longitudinal member and the second longitudinal member increases from the first fastener toward the base.

In some example embodiment, the force transmitting frame is shaped such that a distance between the first longitudinal member to the second longitudinal member is based on:

$$h(x) = \frac{F(L-x)}{T - F\sin\left(\operatorname{atan}\left(\frac{d}{dx}p(x)\right)\right)},$$

wherein h(x) denotes the distance between the first longitudinal member and the second longitudinal member, F denotes a magnitude of a force applied to one end portion of the force transmitting frame, T denotes a magnitude of a tensile force applied to the first longitudinal member, L denotes a length of the force transmitting frame, x denotes a distance from the base of the force transmitting frame to a predetermined point of the second longitudinal member, and p(x) denotes a height of the first longitudinal member at a position the distance x away from the base.

In some example embodiment, the force transmitting frame may further include at least one distance maintaining member between the first longitudinal member and the second longitudinal member, the at least one distance maintaining member configured to maintain a distance between the first longitudinal member and the second longitudinal member.

In some example embodiment, a height of the at least one distance maintaining member increases in a direction away from the first fastener.

In some example embodiment, the force transmitting frame may further include a third longitudinal member connected to the base; a fourth longitudinal member configured to slide with respect to the base; a second fastener configured to fasten a first end of the third longitudinal member to a first end of the fourth longitudinal member; and a fastening member configured to connect the first fastener and the second fastener.

In some example embodiment, the second longitudinal member and the third longitudinal member are on opposite sides of the first longitudinal member, and the fourth longitudinal member and the first longitudinal member are on opposite sides of the third longitudinal member.

In some example embodiment, the force transmitting frame is configured to support a foot of a user, the foot of the user including a rearfoot, a midfoot and a forefoot, the base is configured to support at least a portion of the rearfoot of the user, the first longitudinal member is configured to support at least a portion of the midfoot of the user, the second longitudinal member is between the first longitudinal member and the ground when the user stands erect on the ground, and the first fastener is configured to support at least a portion of the forefoot of the user.

Other example embodiments relate to a motion assistance apparatus.

In some example embodiments, the motion assistance apparatus may include a supporting frame configured to support a first portion of a user; a joint assembly configured to assist a motion of a joint of the user; and a force transmitting frame configured to transmit a force to a second portion of the user, the force transmitting frame including, a base connected to the joint assembly, a first longitudinal member connected to the base, a second longitudinal member configured to slide with respect to the base, and a fastener configured to fasten a first end of the first longitudinal member to a first end of the second longitudinal member.

In some example embodiment, the force transmitting frame may further include at least one distance maintaining member between the first longitudinal member and the second longitudinal member, the at least one distance maintaining member configured to maintain a distance between the first longitudinal member and the second longitudinal member.

In some example embodiment, the motion assistance apparatus may further include an actuator configured to transmit a power to the second longitudinal member; and a power transmitting cable configured to connect the actuator and the force transmitting frame.

In some example embodiment, the actuator may include an elastic body configured to provide an elastic force to the second longitudinal member; and an elastic body support connected to the joint assembly, the elastic body support configured to support the elastic body.

In some example embodiment, the actuator may further include a slider configured to slide with respect to the elastic body support, wherein the power transmitting cable is configured to connect the slider and the second longitudinal member, and the elastic body is between the elastic body support and the slider.

In some example embodiment, the actuator may include a driving source; and a rotary body connected to the driving source, the rotary body configured to wind and unwind the power transmitting cable.

In some example embodiment, the motion assistance apparatus may further include a reducer between the actuator and the second longitudinal member, the reducer configured to increase the power transmitted from the actuator to the second longitudinal member.

In some example embodiment, the reducer may include a first movable pulley associated with the second longitudinal member, and the power transmitting cable may include a first end portion, a second end portion and a middle portion therebetween, the first end portion being connected to the base, the second end portion is connected to the actuator, and the middle portion being wound around the first movable pulley.

In some example embodiment, the force transmitting frame may further include a third longitudinal member parallel to the second longitudinal member, and the first longitudinal member may include a first branch and a second branch, the first branch having one end fastened to the second longitudinal member and the second branch having one end fastened to the third longitudinal member.

In some example embodiment, the motion assistance apparatus may further include an actuator configured to transmit a power to the second longitudinal member and the third longitudinal member; and a reducer configured to increase the power, and to transmit the increased power to each of the second longitudinal member and the third longitudinal member.

In some example embodiment, the reducer may include a fixed pulley associated with the base; a first movable pulley associated with the second longitudinal member; a second movable pulley associated with the third longitudinal member; a first power transmitter including a first end portion, a second end portion and a middle portion therebetween, the first end portion of the first power transmitter being connected to the actuator, the second end portion of the first power transmitter being connected to the base, and the middle portion of the first power transmitter being wound sequentially around the first movable pulley, the fixed pulley, and the second movable pulley; and a second power transmitter including a first end portion, a second end portion and a middle portion therebetween, the first end portion of the second power transmitter being connected to the actuator, the second end portion of the second power transmitter being connected to the base, and the middle portion of the second power transmitter being wound sequentially around the second movable pulley, the fixed pulley, and the first movable pulley.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
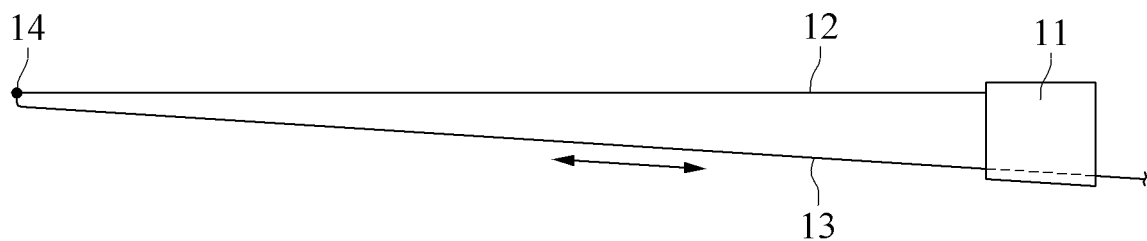
FIG. 1 is a side view illustrating a force transmitting frame according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 2:
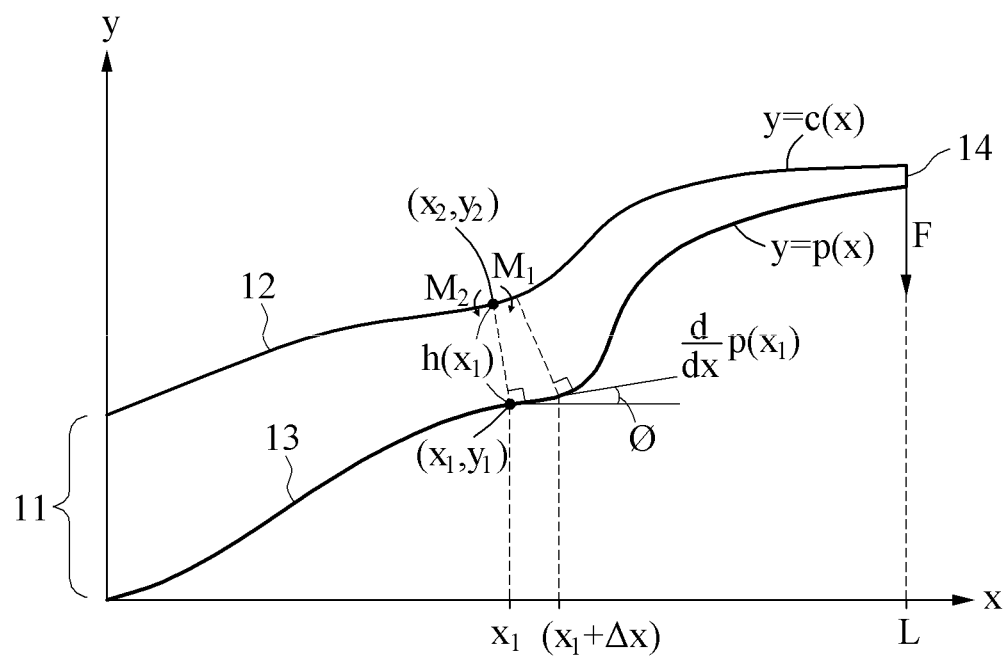
FIG. 2 is a graph illustrating a method of determining a distance between a first longitudinal member and a second longitudinal member according to at least one example embodiment.

FIG. 1 is a side view illustrating a force transmitting frame according to at least one example embodiment, and FIG. 2 is a graph illustrating a method of determining a distance between a first longitudinal member and a second longitudinal member according to at least one example embodiment.

Referring to FIGS. 1 and 2, a force transmitting frame 1 may transmit a force to a portion of a user. The user may correspond to a human, an animal, or a robot. However, the user is not limited thereto. For example, the force transmitting frame 1 may support a sole of a human. In another example, when the force transmitting frame 1 is used as an arm of a robot, the force transmitting frame 1 may transmit a force to an object connected to the arm of the robot. The force transmitting frame 1 may include any form that transmits a force between elements connected to both ends of the force transmitting frame 1, and the purpose of use thereof is not limited thereto. The force transmitting frame 1 may include a base 11, a first longitudinal member 12, a second longitudinal member 13, and a first fastener 14.

A first end portion of the first longitudinal member 12 may be fastened to a first end portion of the second longitudinal member 13. For example, as illustrated in at least FIG. 1, the first longitudinal member 12 and the second longitudinal member 13 may be fastened together as first terminal ends thereof. A second end portion of the first longitudinal member 12 may be fixed to the base 11, and a second end portion of the second longitudinal member 13 may slide with respect to the base 11. For example, the base 11 may include a hole or groove through which the second longitudinal member 13 may pass. The hole or groove may guide the second longitudinal member 13 to slide with respect to the base 11 in a desired (or, alternatively, a predetermined) direction.

A middle region of the second longitudinal member 13 may move relative to a middle region of the first longitudinal member 12. A remaining portion of the second longitudinal member 13 excluding the first end portion thereof may not be fastened to the first longitudinal member 12. The first longitudinal member 12 and the second longitudinal member 13 may each include a thin, elastic board, for example, a material of plastic or steel.

The first fastener 14 may fasten the first end portion of the first longitudinal member 12 and the first end portion of the second longitudinal member 13. For example, the first fastener 14 may be a bolt and a nut, or a string to be used to fasten the first end portion of the first longitudinal member 12 and the first end portion of the second longitudinal member 13.

A distance between the first longitudinal member 12 and the second longitudinal member 13 may increase in a direction away from the first fastener 14. The distance between the first longitudinal member 12 and the second longitudinal member 13 may be determined, for example, as shown in the graph of FIG. 2. The origin of the graph of FIG. 2 corresponds to a portion of the base 11 through which the second longitudinal member 13 may pass. For example, the portion corresponding to the origin may be a hole or groove of the base 11 through which the second longitudinal member 13 may pass. When F denotes a force applied to the first fastener 14, the force F may be a force applied to toes when the user performs a toe-off motion. h(x) that reduces (or, alternatively, prevents) buckling of the first longitudinal member 12 when a set (or, alternatively, a predetermined) force F is applied to the first fastener 14 may be determined. That is, the distance h(x) may make a sum of moments applied to the first longitudinal member 12 be equal to zero.

A point of the first longitudinal member 12 that meets a normal at a point $(x_1, y_1)$ of the second longitudinal member 13 may be denoted as $(x_2, y_2)$. Moments applied to the point $(x_2, y_2)$ may be a moment $M_1$ by the force F, and a moment $M_2$ by a tensile force T applied to an inner plate. Meanwhile, a tensile force applied to the first longitudinal member 12 does not apply a moment to the point $(x_2, y_2)$, and thus may not need to be considered. The moments $M_1$ and $M_2$ may be given as expressed in Equations 1 and 2, respectively.

$$M_1 = F(L - x_1 + h(x_1)\sin \Phi) \qquad \text{[Equation 1]}$$

$$M_2 = Th(x_1) \qquad \text{[Equation 2]}$$

$h(x_1)$ that makes a sum of the moments applied to the point $(x_2, y_2)$ be equal to zero may be determined as expressed by Equation 3. That is, under the condition that the moments $M_1$ and $M_2$ are equal, $h(x_1)$ may be determined as expressed by Equation 3.

$$h(x_1) = \frac{F(L - x_1)}{T - F\sin\Phi} \qquad \text{[Equation 3]}$$

In Equation 3, $\Phi$ denotes an angle between a tangent at a point of the second longitudinal member 13 and an x axis. Meanwhile, when p(x) denotes a height of the second longitudinal member 13, p(x) may be a function that defines a shape of the second longitudinal member 13. $\Phi$ and p(x) may have a relationship as expressed by Equation 4.

$$\tan\Phi = \frac{d}{dx}p(x) \qquad \text{[Equation 4]}$$

Using Equation 4, Equation 3 may be rearranged as expressed by Equation 5.

$$h(x_1) = \frac{F(L-x_1)}{T - F\sin\left(\operatorname{atan}\left(\frac{d}{dx}p(x_1)\right)\right)} \quad \text{[Equation 5]}$$

Equation 5 may be generalized to an equation with respect to a desired (or, alternatively, a predetermined) point (x, y) of the second longitudinal member 13, as expressed by Equation 6.

$$h(x) = \frac{F(L-x)}{T - F\sin\left(\operatorname{atan}\left(\frac{d}{dx}p(x)\right)\right)} \quad \text{[Equation 6]}$$

Here, a relationship between T and F may be calculated when the function p(x) related to the shape of the second longitudinal member 13 is provided. F is a force applied to a portion of the user, and a value of F may be set (or, alternatively, predetermined) by the user or a designer. Thus, when the function p(x) is provided, a shape of the first longitudinal member 12, which is the distance h(x) spaced apart from the second longitudinal member 13, may be determined.

The force transmitting frame 1 determined as described above may transmit a force wholly without being bent although the force is applied to the first fastener 14. When the force transmitting frame 1 is determined based on Equation 6, the force transmitting frame 1 is supposed to transmit the force wholly without being bent in theory. However, in practice, when considering deformation by various factors, for example, a manufacturing tolerance and an assembly tolerance between components of the force transmitting frame 1, the force transmitting frame 1 may be deformed slightly when a force is applied to the first fastener 14. Even in view of such effects, it is learned that both end portions of the force transmitting frame 1 may be stiffer than the middle region of the force transmitting frame 1 with respect to the force.

In a case in which the force transmitting frame 1 has a two-dimensional (2D) shape, the distance between the first longitudinal member 12 and the second longitudinal member 13 may be determined in proportion to the distance to the first fastener 14 in a direction perpendicular to a direction in which the force is applied to the first fastener 14. That is, the distance between the first longitudinal member 12 and the second longitudinal member 13 may increase from the first fastener 14 toward the base 11.

Meanwhile, the above description is merely an example of a method of determining the distance between the first longitudinal member 12 and the second longitudinal member 13, and thus example embodiments are not limited thereto.

Figure 3A:
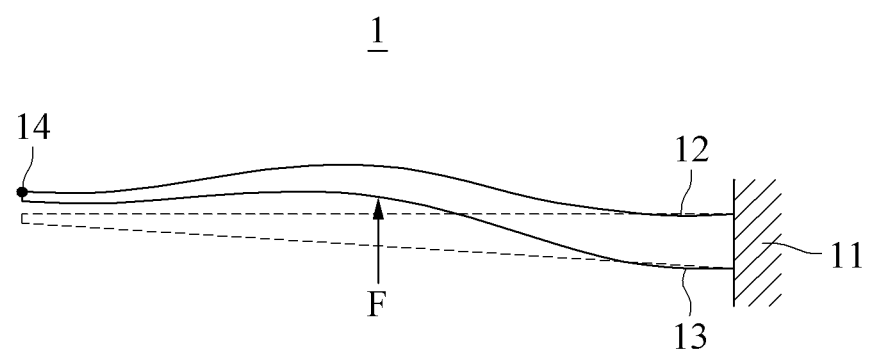
FIGS. 3A through 3C illustrate a force transmitting frame that is deformed when a load is applied to the force transmitting frame according to at least one example embodiment.
Figure 3B:
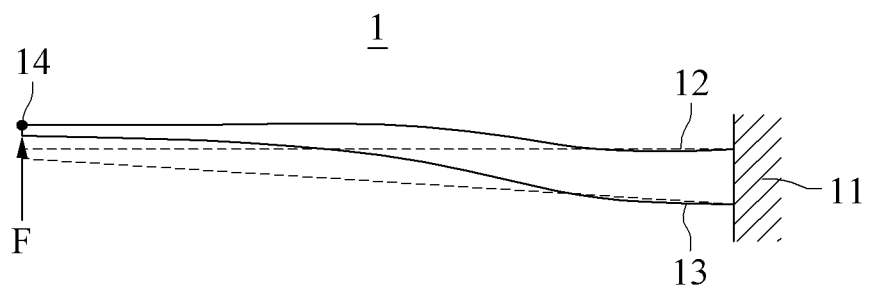
Figure 3C:
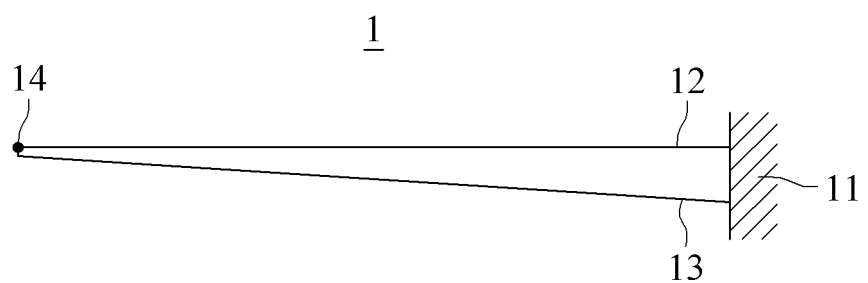

FIGS. 3A through 3C illustrate a force transmitting frame that is deformed when a load is applied to the force transmitting frame according to at least one example embodiment.

In detail, FIG. 3A illustrates a case in which a force is applied to the middle region of the force transmitting frame 1, FIG. 3B illustrates a case in which a force is applied to one end portion of the force transmitting frame 1, and FIG. 3C illustrates a case in which a load is not applied to the force transmitting frame 1.

When the distance between the first longitudinal member 12 and the second longitudinal member 13 is determined based on Equation 6, both end portions of the force transmitting frame 1 may be stiffer than the middle region of the force transmitting frame 1. Referring to FIG. 3A, when the same load F is applied to the middle region of the force transmitting frame 1, a position of the middle region of the force transmitting frame 1 may change greatly. Referring to FIG. 3B, when the force F is applied to an end portion of the force transmitting frame 1, a position of the end portion of the force transmitting frame 1 may not change greatly.

Figure 4A:
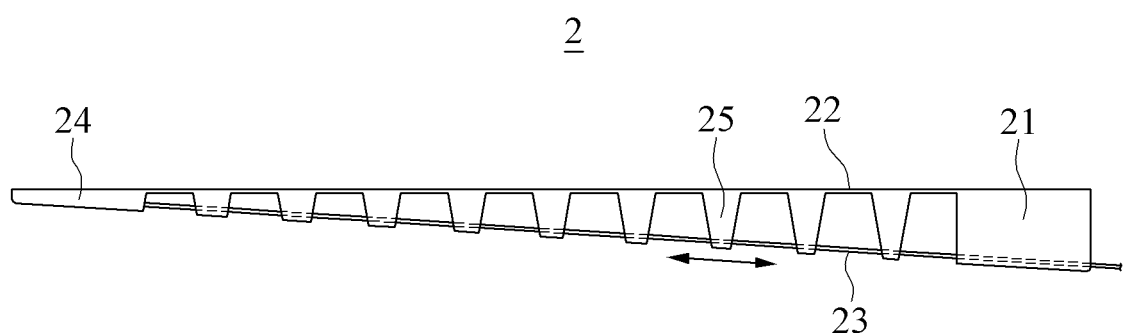
FIG. 4A illustrates a force transmitting frame according to at least one example embodiment.
Figure 4B:
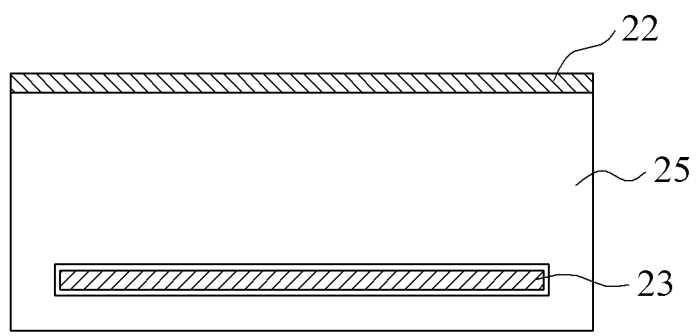
FIG. 4B is a cross-sectional view illustrating a force transmitting frame according to at least one example embodiment.

FIG. 4A illustrates a force transmitting frame according to at least one example embodiment, and FIG. 4B is a cross-sectional view illustrating the force transmitting frame according to at least one example embodiment.

Referring to FIGS. 4A and 4B, a force transmitting frame 2 may include a base 21, a first longitudinal member 22, a second longitudinal member 23, a first fastener 24, and at least one distance maintaining member 25.

The distance maintaining member 25 may be disposed between the first longitudinal member 22 and the second longitudinal member 23 to maintain a distance between the first longitudinal member 22 and the second longitudinal member 23. The distance maintaining member 25 may have a hole or groove through which the second longitudinal member 23 may pass. The hole or groove may guide the second longitudinal member 23 to be in contact with the distance maintaining member 25 and slide in a desired (or, alternatively, a predetermined) direction. The distance maintaining member 25 may be fixed to one of the first longitudinal member 22 and the second longitudinal member 23. A height of the distance maintaining member 25 may be determined to be the distance between the first longitudinal member 12 and the second longitudinal member 13 of FIGS. 1 and 2.

Figure 5:
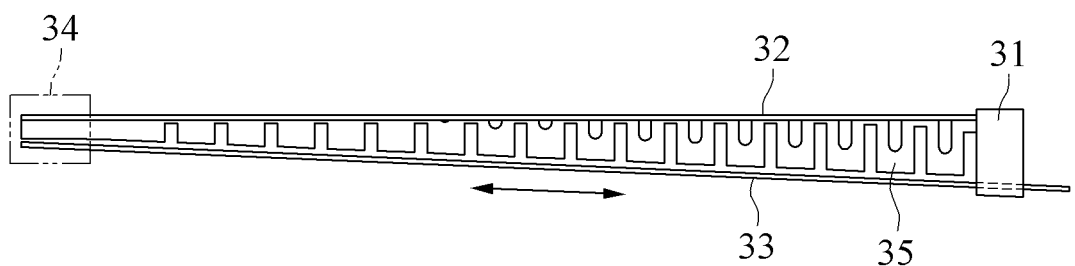
FIG. 5 is a side view illustrating a force transmitting frame according to at least one example embodiment.

FIG. 5 is a side view illustrating a force transmitting frame according to at least one example embodiment.

Referring to FIG. 5, a force transmitting frame 3 may include a base 31, a first longitudinal member 32, a second longitudinal member 33, a first fastener 34, and a distance maintaining member 35.

The distance maintaining member 35 may include a plurality of grooves formed in a vertical direction. In another example, the distance maintaining member 35 may have a shape being bent multiple times in a vertical direction. For example, the distance maintaining member 35 may have a shape of a sine wave, a square wave, or a zigzag.

Figure 6:
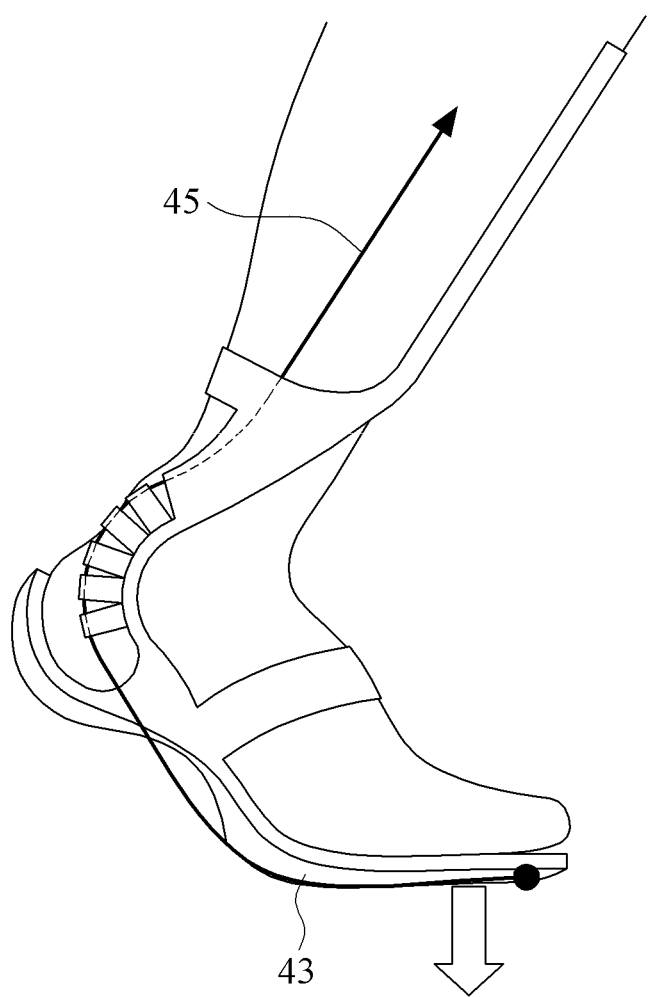
FIG. 6 illustrates a motion assistance apparatus that assists a toe-off motion of a user according to at least one example embodiment.

FIG. 6 illustrates a motion assistance apparatus that assists a toe-off motion of a user according to at least one example embodiment.

Referring to FIG. 6, a motion assistance apparatus 4 may be worn by a user to assist a motion of the user. The user may correspond to a human, an animal, or a robot. However, the user is not limited thereto. The motion assistance apparatus 4 may include a force transmitting frame 43, and a power transmitting cable 45. FIG. 6 exemplarily illustrates a case in which the motion assistance apparatus 4 assists a motion of a foot of the user. However, the motion assistance apparatus 4 may also assist a motion of another portion in an upper body, for example, a wrist, an elbow, or a shoulder of the user, or a motion of another portion in a lower body, for example, a knee or a hip joint of the user. That is, the motion assistance apparatus 4 may assist a motion of a portion of the user.

The force transmitting frame 43 may be flexible and thus, may be bent flexibly in response to a bending motion of a sole in a process before and after a terminal stance phase.

Further, both end portions of the force transmitting frame 43 may be stiffer than a middle region of the force transmitting frame 43. Thus, a front end portion of the force transmitting frame 43 may push the ground strongly by a tensile force transmitted through the power transmitting cable 45 connected to the force transmitting frame 43, whereby the motion assistance apparatus 4 may assist a toe-off motion of the user.

Detailed examples of the motion assistance apparatus 4 will be described hereinafter.

Figure 7:
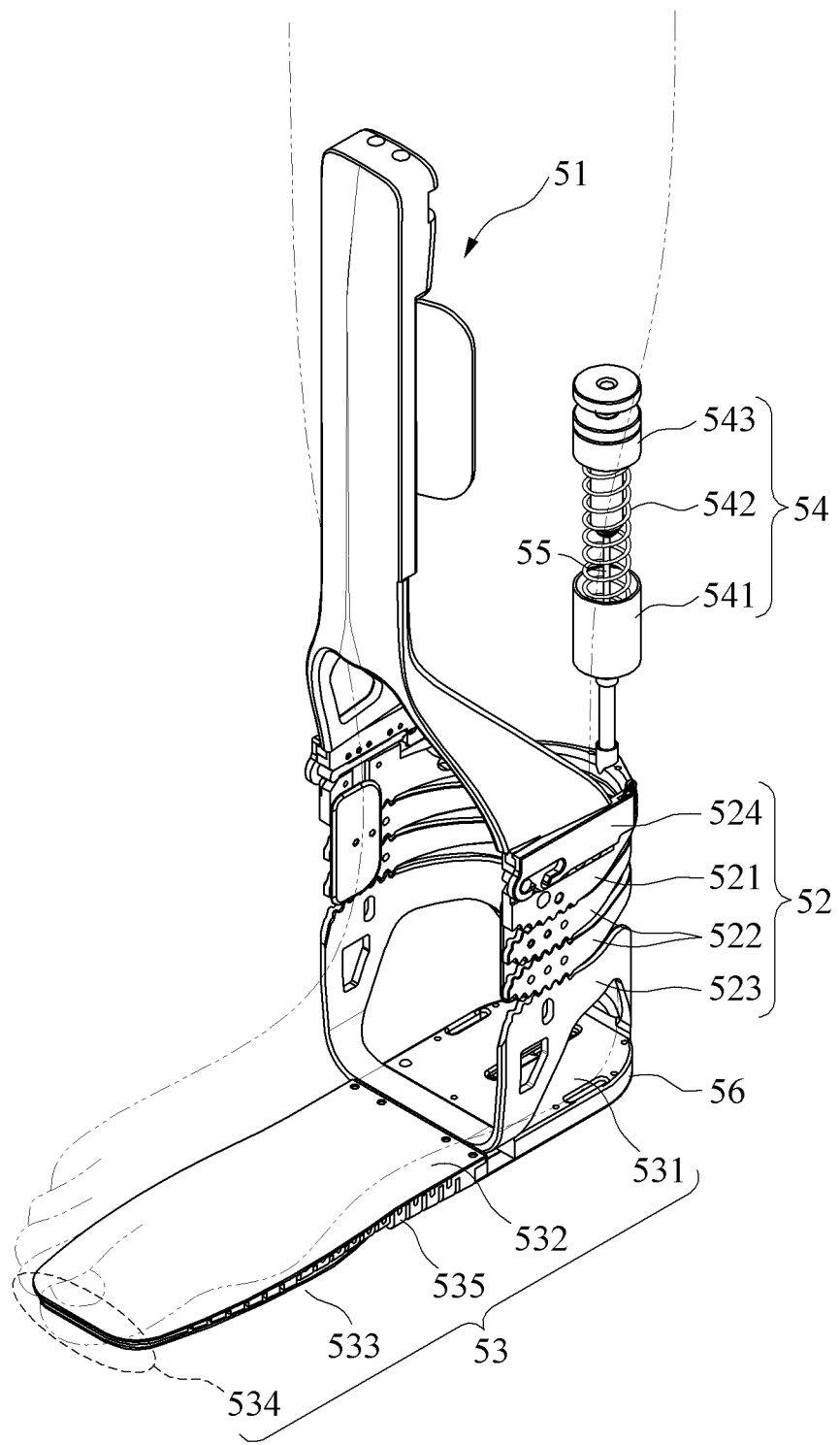
FIG. 7 is a perspective view illustrating a motion assistance apparatus according to at least one example embodiment.
Figure 8:
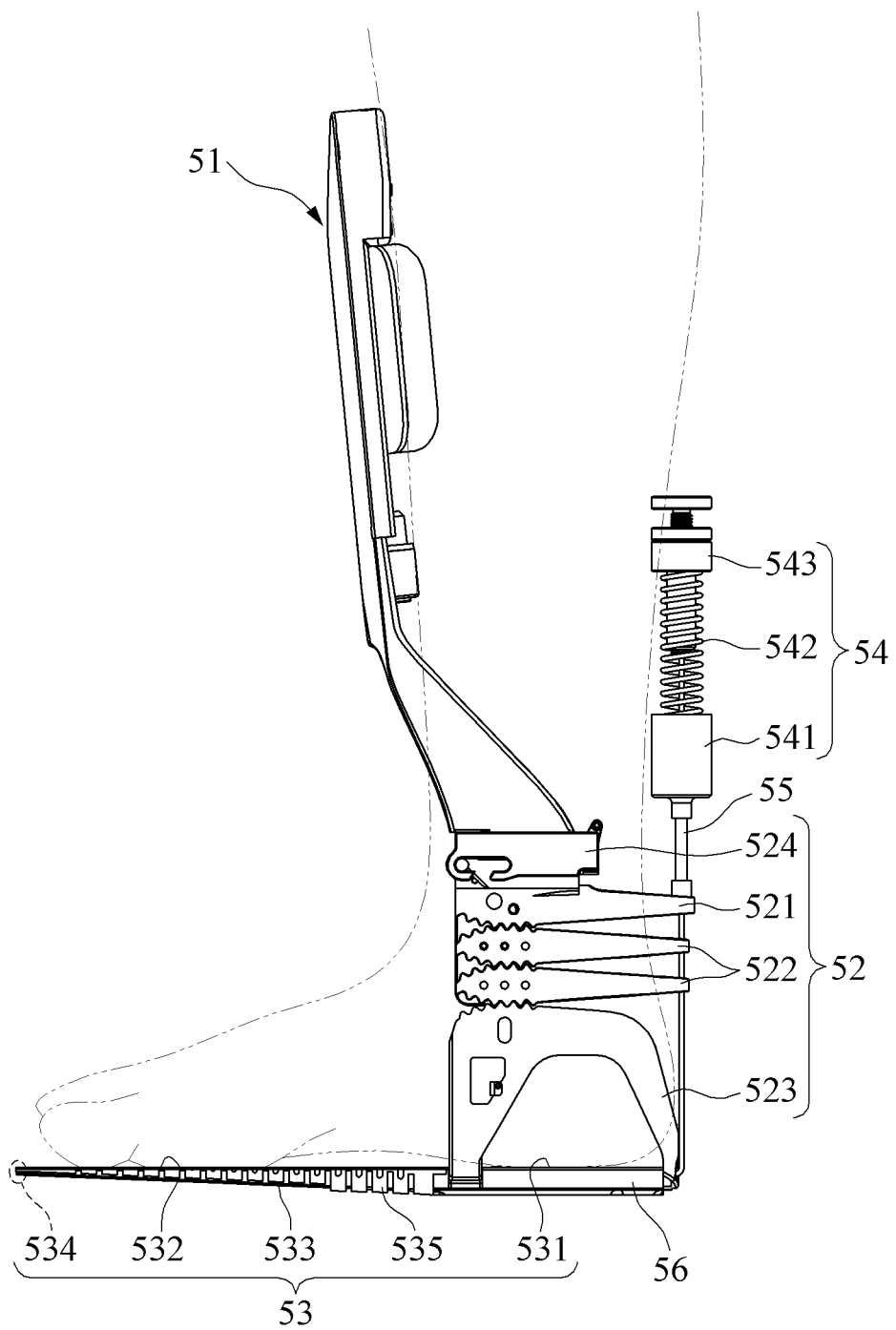
FIG. 8 is a side view illustrating a motion assistance apparatus according to at least one example embodiment.
Figure 9:
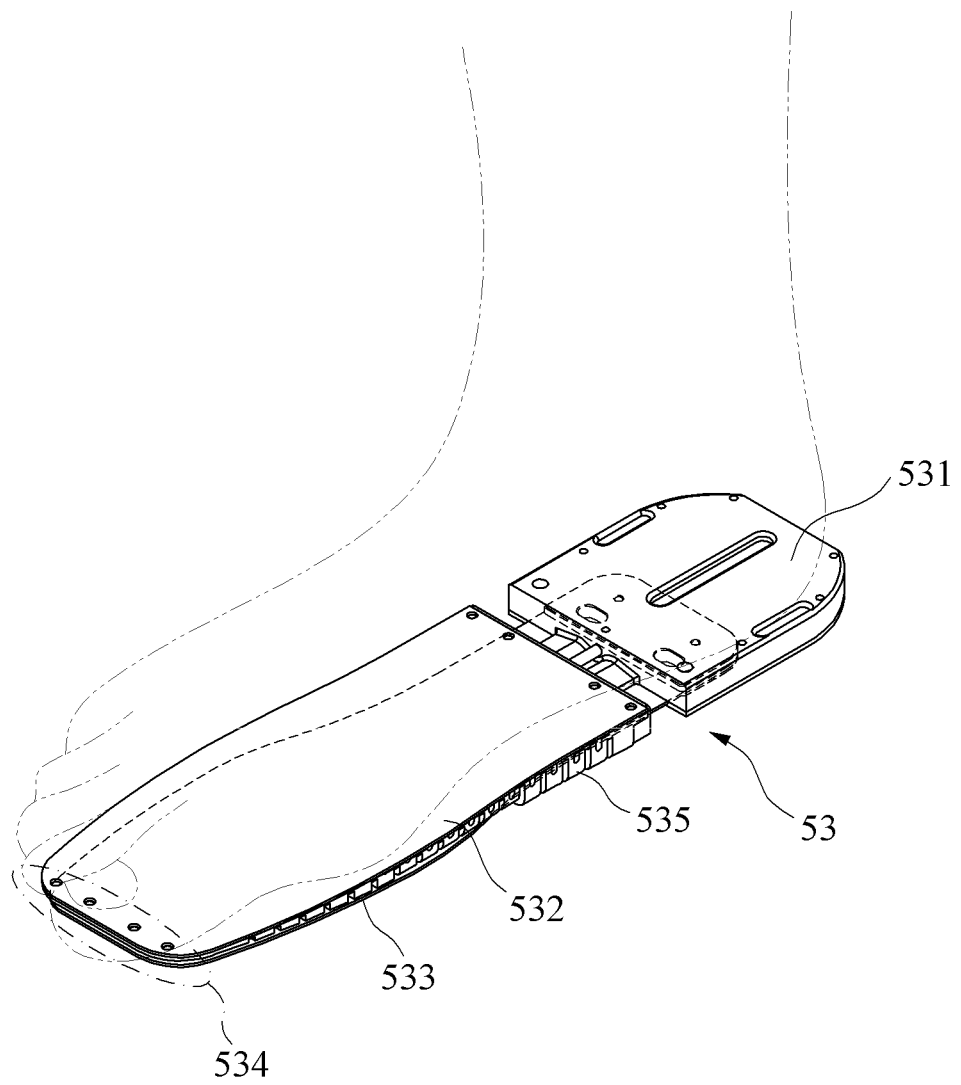
FIG. 9 is a perspective view illustrating a force transmitting frame according to at least one example embodiment.

FIG. 7 is a perspective view illustrating a motion assistance apparatus according to at least one example embodiment, FIG. 8 is a side view illustrating the motion assistance apparatus according to at least one example embodiment, and FIG. 9 is a perspective view illustrating a force transmitting frame according to at least one example embodiment.

Referring to FIGS. 7 and 9, a motion assistance apparatus 5 may include a supporting frame 51, a joint assembly 52, a force transmitting frame 53, an actuator 54, a power transmitting cable 55, and a reducer 56.

The supporting frame 51 and the force transmitting frame 53 may be disposed on opposite sides of a joint of a user to support the user. For example, in a case in which the motion assistance apparatus 5 assists a motion of an ankle of the user, the supporting frame 51 and the force transmitting frame 53 may be disposed on opposite sides of the ankle of the user. The supporting frame 51 may support a portion above the ankle of the user, for example, a calf, and the force transmitting frame 53 may support a portion below the ankle of the user, for example, a foot.

The supporting frame 51 may be provided in a structure that partially encloses a portion of the user to reduce a probability of (or, alternatively, prevent) a separation of the user. The supporting frame 51 may include, for example, a detachable belt to support the entire circumference of the calf of the user. A lower end of the supporting frame 51 may be connected to the joint assembly 52.

The joint assembly 52 may assist a motion of a joint of the user. The joint assembly 52 may assist a dorsi-flexion or plantar-flexion motion of a talocrural joint of the user. That is, the joint assembly 52 may enable the supporting frame 51 to rotate relative to the force transmitting frame 53. The joint assembly 52 may include a cover frame 521, a middle frame 522, a bottom frame 523, and a cover connector 524.

The cover frame 521, the middle frame 522, and the bottom frame 523 that are arranged in a row may be provided in a U-shape that encloses the ankle of the user.

Bottom surfaces of both ends of the cover frame 521 may include contact surfaces, and the contact surfaces may be formed based on a desired (or, alternatively, a predetermined) curvature. The contact surfaces may include a repetitive gear tooth shape of a desired (or, alternatively, a predetermined) size, and the curvature may be applied to a base circle of the gear tooth shape.

Both ends of the middle frame 522 may include contact surfaces, and the contact surfaces may be formed based on a desired (or, alternatively, a predetermined) curvature. The contact surfaces may include a repetitive gear tooth shape of a desired (or, alternatively, a predetermined) size, and the curvature may be applied to a base circle of the gear tooth shape. Although FIG. 7 illustrates a case in which a plurality of middle frames 522 are provided, a single middle frame 522 may be provided, or the cover frame 521 may be connected directly to the bottom frame 523 without a middle frame 522. Two neighboring middle frames of the plurality of middle frames 522 may each have contact portions that engage with those of the other.

Top surfaces of both ends of the bottom frame 523 may include contact surfaces, and the contact surfaces may be formed based on a desired (or, alternatively, a predetermined) curvature. The contact surfaces may include a repetitive gear tooth shape of a desired (or, alternatively, a predetermined) size, and the curvature may be applied to a base circle of the gear tooth shape.

The gear tooth shape formed on the contact surfaces of the cover frame 521 may engage with the gear tooth shape formed on the contact surfaces of the middle frame 522. The gear tooth shape formed on the contact surfaces of the bottom frame 523 may engage with the gear tooth shape formed on the contact surfaces of the middle frame 522.

The cover connector 524 may connect the cover frame 521 and the supporting frame 51 such that the cover frame 521 and the supporting frame 51 may rotate relative to each other about an axis corresponding to a longitudinal direction of the foot of the user. In the above structure, the force transmitting frame 53 may rotate in response to an inversion or eversion motion of the user, whereby the user wearability may improve.

The force transmitting frame 53 may transmit a force to a second portion of the user that is connected through at least one joint to a first portion of the user that is supported by the supporting frame 51. For example, in a case in which the supporting frame 51 supports the calf of the user, the force transmitting frame 53 may transmit a force to a sole of the user. The force transmitting frame 53 may include a base 531 configured to support at least a portion of a rearfoot of the user, a first longitudinal member 532 configured to support at least a portion of a midfoot of the user, a second longitudinal member 533 with a first end portion fastened to the first longitudinal member 532 and a second end portion configured to slide with respect to the base 531, a fastener 534 configured to support at least a portion of a forefoot of the user, and a distance maintaining member 535 configured to maintain a distance between the first longitudinal member 532 and the second longitudinal member 533.

The force transmitting frame 53 may have a shape determined based on Equation 6. For example, the force transmitting frame 53 may have a shape with a length greater than a width to support from the forefoot to the rearfoot of the user. A middle region of the force transmitting frame 53 to be in contact with the midfoot of the user may be flexible to improve the user wearability. Meanwhile, a first end portion of the force transmitting frame 53 that receives a force from the power transmitting cable 55 and a second end portion of the force transmitting frame 53 that transmits the force to the forefoot of the user may be stiffer than the middle region of the force transmitting frame 53, and thus the force transmitting frame 53 may sufficiently transmit the force from the power transmitting cable 55 to the forefoot of the user.

The actuator 54 may provide a force to the second longitudinal member 533, thereby assisting a push-off motion of the user. When the actuator 54 pulls the second longitudinal member 533, the second longitudinal member 533 may be bent to push up the rearfoot of the user from the ground (a heel-off motion). Then, the second longitudinal member 533 may be restored by a tensile force applied to the second longitudinal member 533, thereby assisting a toe-off motion of the user. For example, the actuator 54 may be a passive actuator using an elastic body as shown in FIGS. 7 through 10, or may be an active actuator using a motor as shown in FIG. 11. Hereinafter, an example of the passive actuator using the elastic body will be described. For example, the actuator 54 may include an elastic body 542, an elastic body support 541 including a receiving space to receive the elastic body 542, and a slider 543. The slider 543 and the elastic body support 541 may be disposed on opposite sides of the elastic body 542.

The elastic body 542 may generate a restoring force by being compressed or stretched before a push-off operation in a stance phase, and returning to an equilibrium state in the push-off operation. For example, a lower end of the elastic body 542 may be fixed to the elastic body support 541. An upper end of the elastic body 542 may be fixed to the slider 543. That is, the elastic body 542 may be disposed between the elastic body support 541 and the slider 543. In the above structure, when a tensile force is applied to the power transmitting cable 55, the slider 543 may slide toward the elastic body support 541 such that the elastic body 542 may be compressed, whereby a potential energy of the elastic body 542 may increase.

The power transmitting cable 55 may connect the actuator 54 and the force transmitting frame 53, and transmit a power therebetween. For example, one end of the power transmitting cable 55 may pass through the elastic body support 541 to be connected to the slider 543, and another end of the power transmitting cable 55 may be connected to the second longitudinal member 533. The power transmitting cable 55 may be, for example, a longitudinal member such as a wire, a cable, a string, a rubber band, a spring, a belt, or a chain.

When the user performs a dorsi-flexion or plantar-flexion motion before the push-off motion, distances between middle regions of the frames 521, 522, and 523 of the joint assembly 52 may increase or decrease such that a distance between the actuator 54 and the force transmitting frame 53 may change. As the distance between the actuator 54 and the force transmitting frame 53 changes, the tensile force applied to the power transmitting cable 55 may change a length of the elastic body 542. In this process, the potential energy of the elastic body 542 may increase, and the increased potential energy may be released to assist the push-off motion of the user when the user performs the push-off motion. The released potential energy may be transmitted to the force transmitting frame 53 through the power transmitting cable 55, and the energy transmitted to the force transmitting frame 53 may pull the rearfoot of the user. Further, the energy transmitted to the force transmitting frame 53 may provide a force to be used for the forefoot of the user to push the ground.

The reducer 56 may increase the power received from the actuator 54 and transmit the increased power to the second longitudinal member 533. The reducer 56 may be disposed between the force transmitting frame 53 and the power transmitting cable 55. The reducer 56 will be described further with reference to FIGS. 12A and 12B.

Figure 10:
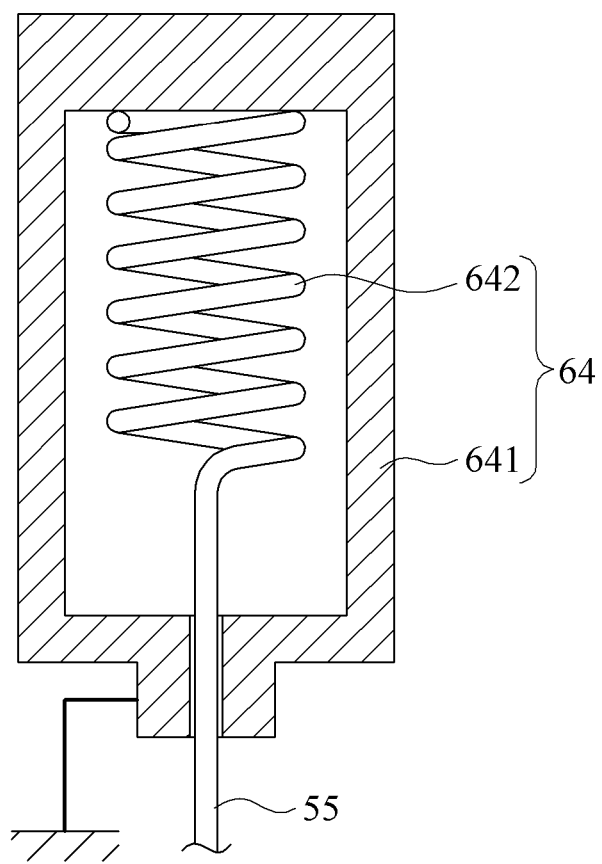
FIG. 10 illustrates an actuator according to at least one example embodiment.
Figure 11:
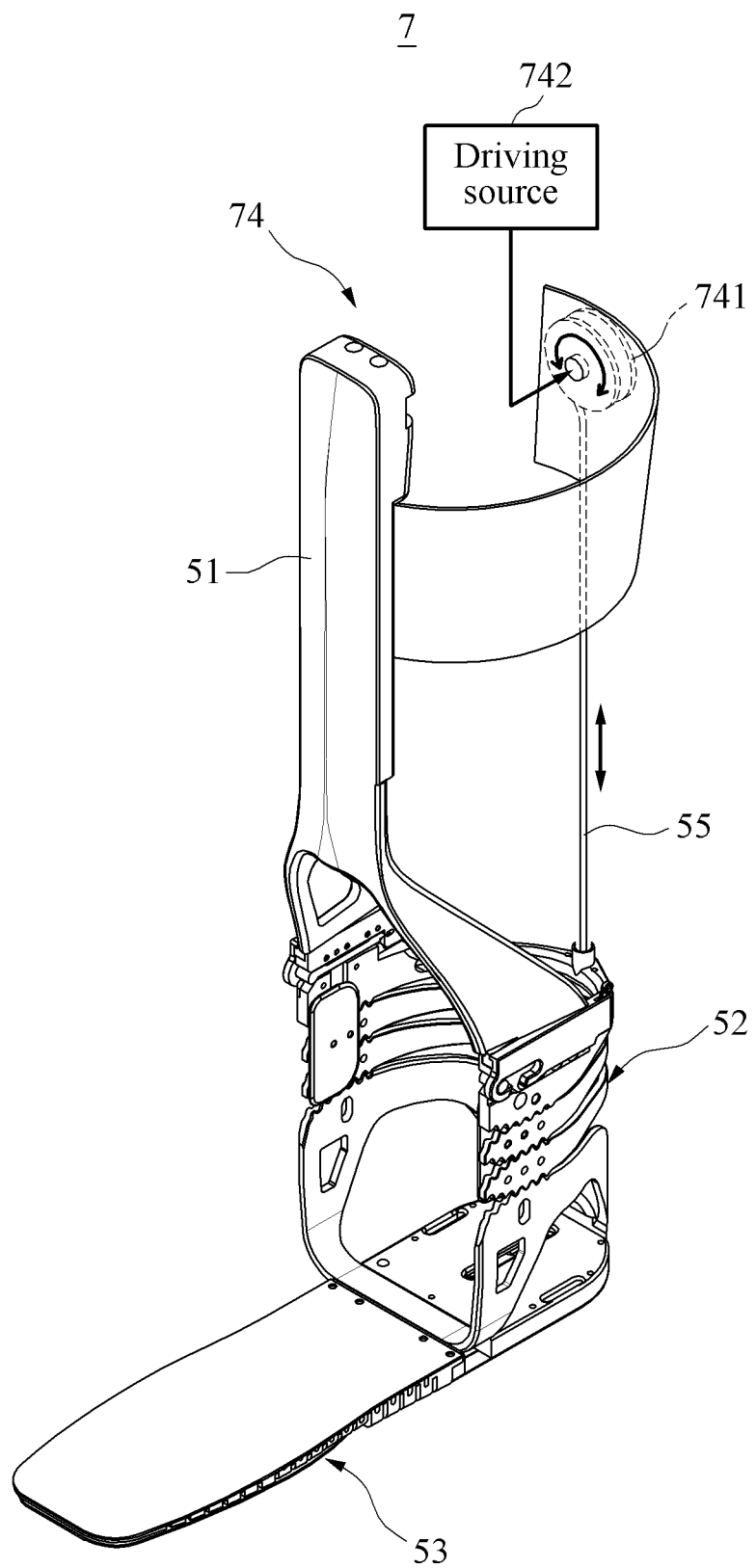
FIG. 11 is a perspective view illustrating a motion assistance apparatus according to at least one example embodiment.

FIG. 10 illustrates an actuator according to at least one example embodiment.

Referring to FIG. 10, an actuator 64 may include an elastic body 642, and an elastic body support 641 including a receiving space to receive the elastic body 642.

For example, a first end portion of the elastic body 642 may be fixed to one side of the receiving space of the elastic body support 641, and a second end portion of the elastic body 642 may be connected to the power transmitting cable 55. In the above structure, when a tensile force is applied to the power transmitting cable 55, the elastic body 542 may elongate and the potential energy of the elastic body 542 may increase.

FIG. 11 is a perspective view illustrating a motion assistance apparatus according to at least one example embodiment.

Referring to FIG. 11, a motion assistance apparatus 7 may include the supporting frame 51, the joint assembly 52, the force transmitting frame 53, an actuator 74, and the power transmitting cable 55.

The actuator 74 may be an active actuator that includes a driving source 742 and a rotary body 741. The power transmitting cable 55 may be disposed between the rotary body 741 and the force transmitting frame 53 to transmit a force therebetween.

The driving source 742 may generate a power to rotate the rotary body 741 using a voltage, a current, and/or a hydraulic pressure. The type of the driving source 742 is not limited thereto. The driving source 742 may be disposed on one side of the supporting frame 51. Meanwhile, the driving source 742 may be disposed on a portion excluding the supporting frame 51, for example, an upper body of the user, and remotely connected to the rotary body 741.

The rotary body 741 may wind or unwind the power transmitting cable 55, thereby transmitting the power to the force transmitting frame 53 through the power transmitting cable 55. The rotary body 741 may be disposed on one side of the supporting frame 51 as shown in FIG. 11. However, the position of the rotary body 741 is not limited thereto.

As discussed above, the actuator 74 may be an active actuator that includes the driving source 742. The motion assistance apparatus 7 may further include additional devices to control the driving source 742.

For example, the motion assistance apparatus 7 may include one or more sensors and a controller (not shown).

The one or more sensors may include one or more pressure sensors on the force transmitting frame 53.

The controller may include a memory and processing circuitry.

The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

The processing circuitry may include a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design and/or execution of computer readable instructions stored in the memory, as a special purpose computer to control the driving source 742 based on signals received from the one or more sensors. For example, the controller may determine whether the user is performing a push-off operation based on data from the one or more sensors, and instruct the driving source 742 to rotate the rotary body 741 in a first direction before the user performs a push-off operation in a stance phase, and instruct the driving source 742 to rotate the rotary body 741 in a second direction when the user is performing the push-off operation.

Figure 12A:
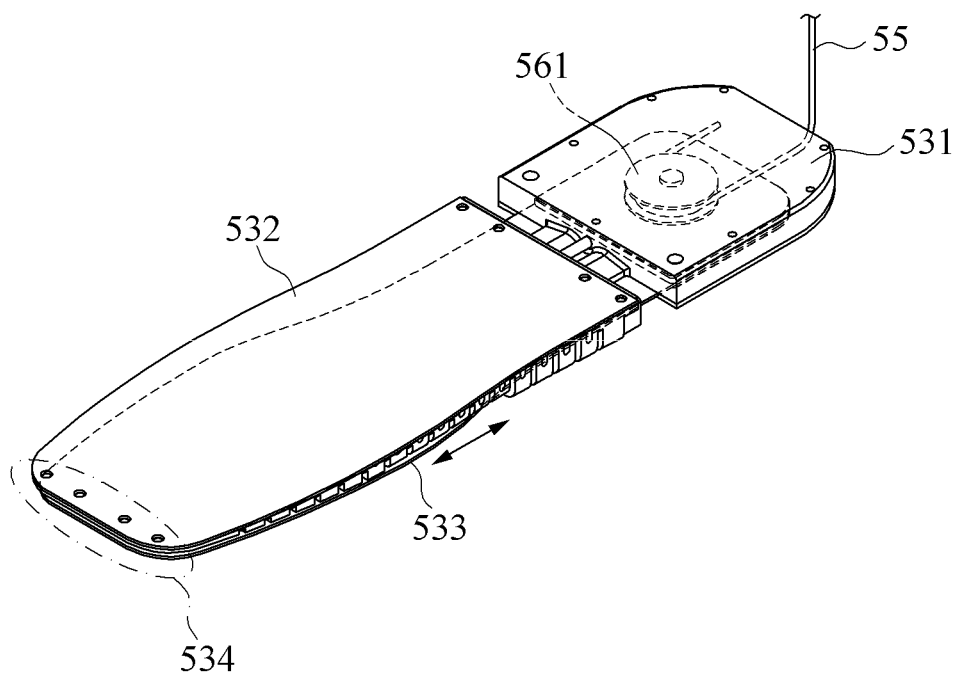
FIGS. 12A and 12B illustrate a reducer according to at least one example embodiment.
Figure 12B:
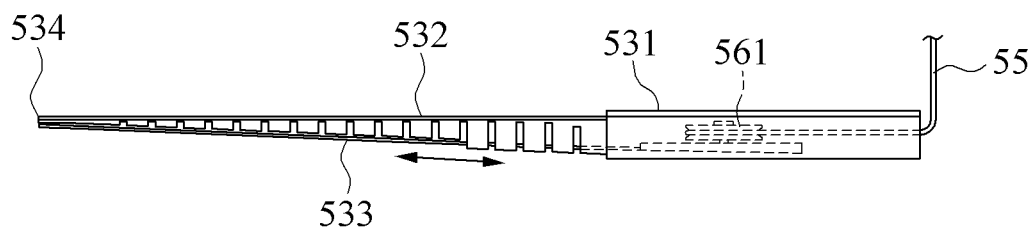

FIGS. 12A and 12B illustrate a reducer according to at least one example embodiment.

Referring to FIGS. 12A and 12B, the reducer 56 may include a movable pulley 561 rotatably provided in the second longitudinal member 533. Similar to the second longitudinal member 533, the movable pulley 561 may slide with respect to the base 531.

A first end portion of the power transmitting cable 55 may be fixed to the base 531, a second end portion of the power transmitting cable 55 may be fixed to an actuator, and a middle portion of the power transmitting cable 55 may be wound around the movable pulley 561. In the above structure, when the actuator applies a tensile force of T to the power transmitting cable 55, a tensile force of, for example, 2T may be applied to the second longitudinal member 533.

Figure 13:
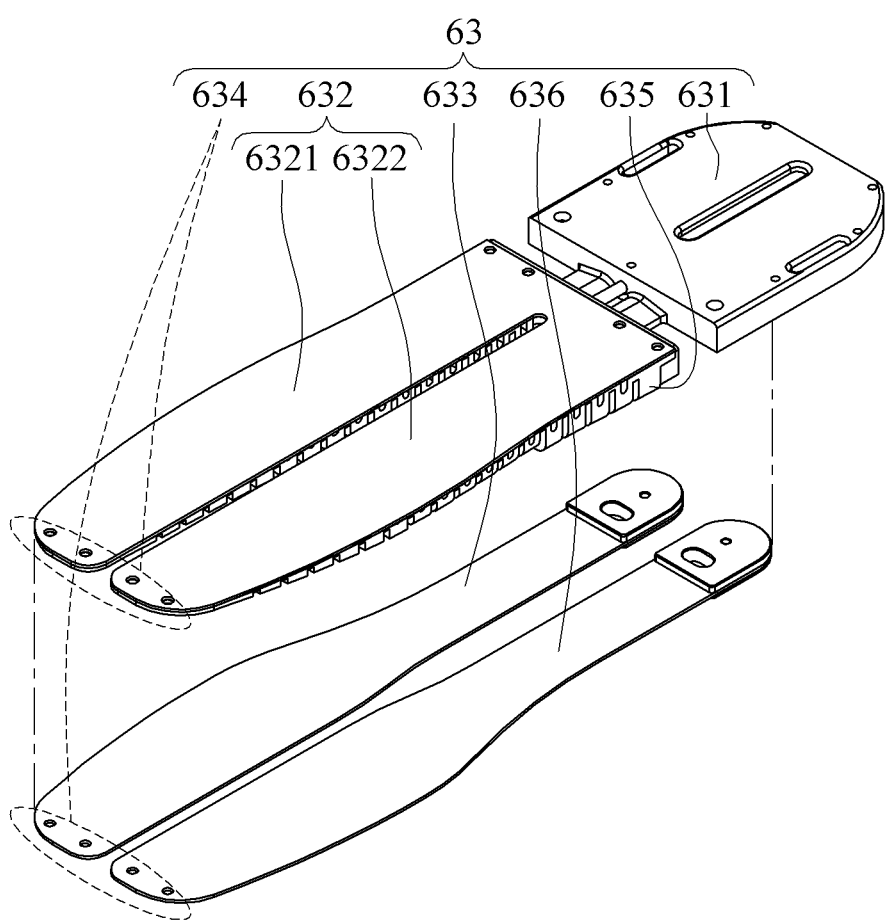
FIG. 13 is an exploded perspective view illustrating a force transmitting frame according to at least one example embodiment.

FIG. 13 is an exploded perspective view illustrating a force transmitting frame according to at least one example embodiment.

Referring to FIG. 13, a force transmitting frame 63 may include a base 631, a first longitudinal member 632, a second longitudinal member 633, a third longitudinal member 636, a fastener 634, and a distance maintaining member 635.

The first longitudinal member 632 may include a first branch 6321 fastened to a first end portion of the second longitudinal member 633, and a second branch 6322 fastened to a first end portion of the third longitudinal member 636.

The third longitudinal member 636 may be disposed parallel to the second longitudinal member 633. Similar to the second longitudinal member 633, the third longitudinal member 636 may slide with respect to the base 631.

In a case in which the force transmitting frame 63 provided in the above structure is used as an insole for a user, the user may experience the improved wearability when performing an inversion or eversion motion since the force transmitting frame 63 is divided into a left portion and a right portion.

Figure 14:
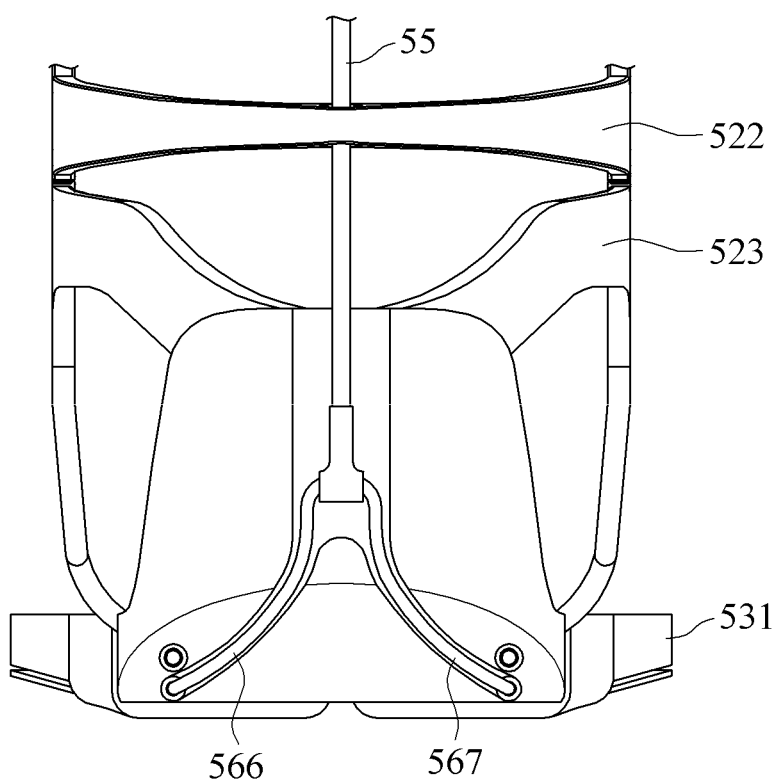
FIG. 14 illustrates a power transmitting cable and a power transmitter according to at least one example embodiment.
Figure 15:
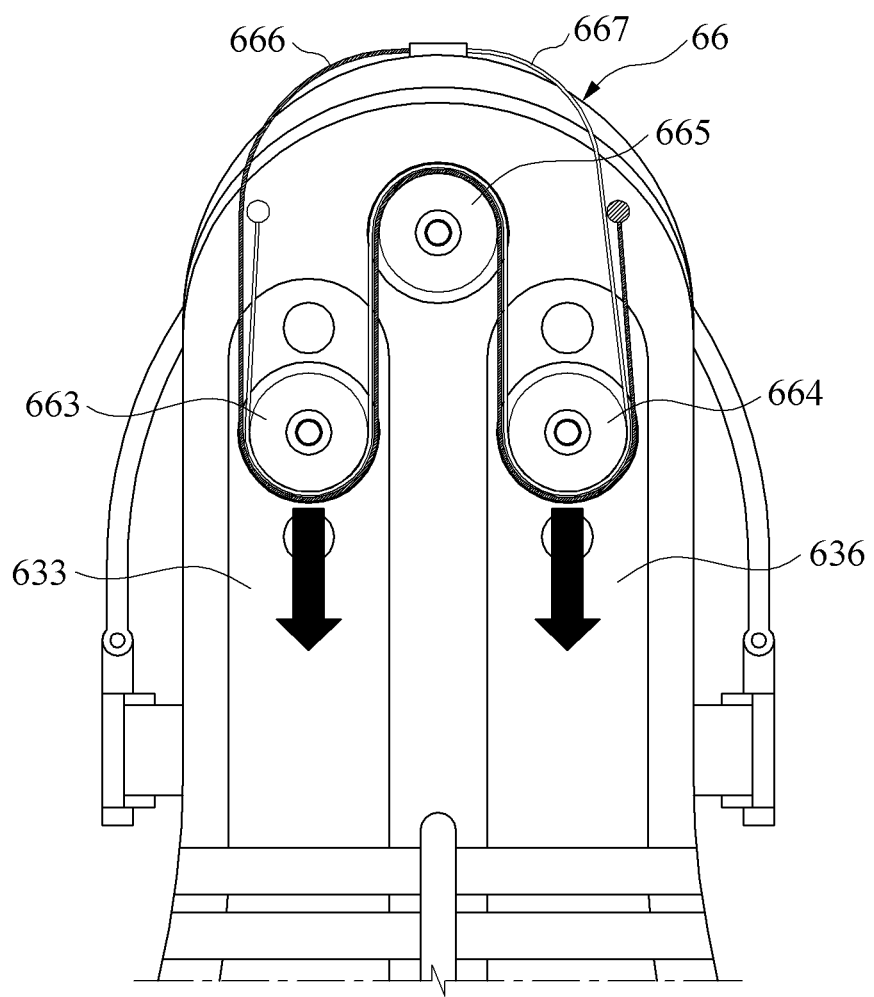
FIG. 15 illustrates a reducer according to at least one example embodiment.

FIG. 14 illustrates a power transmitting cable and a power transmitter according to at least one example embodiment, and FIG. 15 illustrates a reducer according to at least one example embodiment.

Referring to FIGS. 14 and 15, a reducer 66 may include a first movable pulley 663 rotatably provided in a second longitudinal member 633, a second movable pulley 664 rotatably provided in a third longitudinal member 636, a fixed pulley 665 provided in a base 631, and a first power transmitter 666 and a second power transmitter 667 connected to the power transmitting cable 55.

The first power transmitter 666 may be wounded sequentially around the first movable pulley 663, the fixed pulley 665, and the second movable pulley 664, and fixed to base 631. The second power transmitter 667 may be wounded sequentially around the second movable pulley 664, the fixed pulley 665, and the first movable pulley 663, and fixed to the base 631.

A tensile force T may be divided into T/2 to be applied to the first power transmitter 666 and T/2 to be applied to the second power transmitter 667. In the above structure, when an actuator applies a tensile force of T to the power transmitting cable 55, a tensile force of, for example, T/2 may be applied to each of the first power transmitter 666 and the second power transmitter 667. Further, according to a working principle of pulley, the first power transmitter 666 may transmit a tensile force of T to each of the first movable pulley 663 and the second movable pulley 664. Similarly, the second power transmitter 667 may transmit a tensile force of T to each of the first movable pulley 663 and the second movable pulley 664. Thus, a tensile force of, for example, 2T may be applied to each of the second longitudinal member 633 and the third longitudinal member 636.

Figure 16:
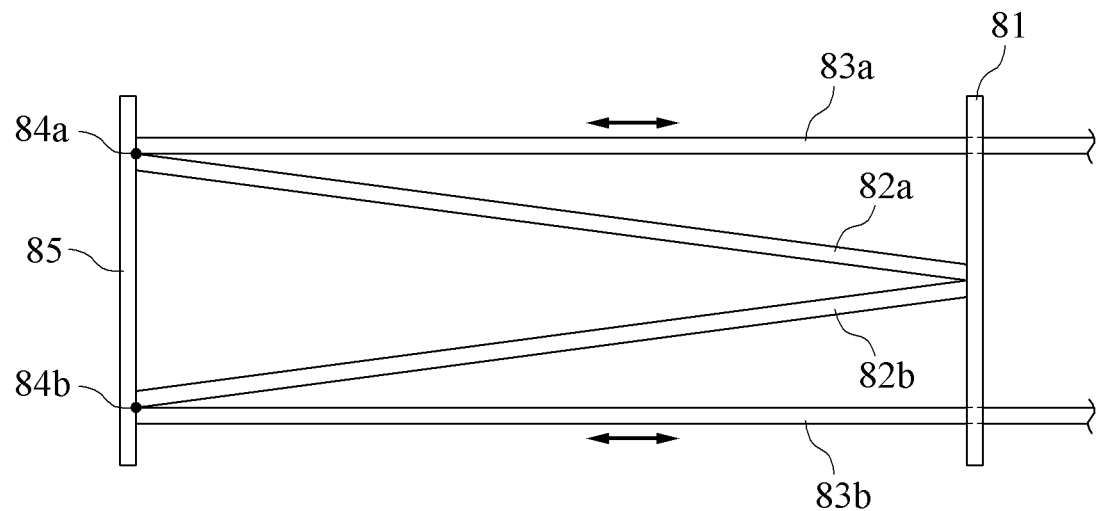
FIG. 16 is a side view illustrating a force transmitting frame according to at least one example embodiment.

FIG. 16 is a side view illustrating a force transmitting frame according to at least one example embodiment.

Referring to FIG. 16, a force transmitting frame 8 may include a base 81, a first longitudinal member 82*a*, a second longitudinal member 83*a*, a third longitudinal member 82*b*, a fourth longitudinal member 83*b*, a first fastener 84*a*, a second fastener 84*b*, and a fastening member 85. The fastening member 85 may connect a first fastener 84*a* that fastens a first end portion of the first longitudinal member 82*a* and a first end portion of the second longitudinal member 83*a* to a second fastener 84*b* that fastens a first end portion of the third longitudinal member 82*b* and a first end portion of the fourth longitudinal member 83*b*.

The first end portion of the first longitudinal member 82*a* may be fastened to the first end portion of the second longitudinal member 83*a*. A second end portion of the first longitudinal member 82*a* may be fixed to the base 81, and a second end portion of the second longitudinal member 83*a* may slide with respect to the base 81.

The first end portion of the third longitudinal member 82*b* may be fastened to the first end portion of the fourth longitudinal member 83*b*. A second end portion of the third longitudinal member 82*b* may be fixed to the base 81, and a second end portion of the fourth longitudinal member 83*b* may slide with respect to the base 81.

For example, the base 81 may include a hole or groove through which the second longitudinal member 83*a* and/or the fourth longitudinal member 83*b* may pass. The hole or groove may guide the second longitudinal member 83*a* and/or the fourth longitudinal member 83*b* to slide with respect to the base 81 in a predetermined direction.

The first longitudinal member 82*a*, the second longitudinal member 83*a*, the third longitudinal member 82*b*, and the fourth longitudinal member 83*b* may each include a thin, elastic board, for example, a material of plastic or steel. In the above structure, both end portions of the force transmitting frame 8 may be stiffer than a middle region of the force transmitting frame 8, similar to the above-described force transmitting frames according to the other example embodiments.

The second longitudinal member 83*a* and the third longitudinal member 82*b* may be disposed on opposite sides of the first longitudinal member 82*a*, and the fourth longitudinal member 83*b* and the first longitudinal member 82*a* may be disposed on opposite sides of the third longitudinal member 82*b*. By disposing the second longitudinal member 83*a* and the fourth longitudinal member 83*b* that may slide with respect to the base 81 to be spaced apart from each other, mutual interference caused by the sliding motion may be minimized and a driving range in which the force transmitting frame 8 is to be bent may improve, when compared to a case of disposing the two longitudinal members 83*a* and 83*b* adjacent to each other.

Figure 17A:
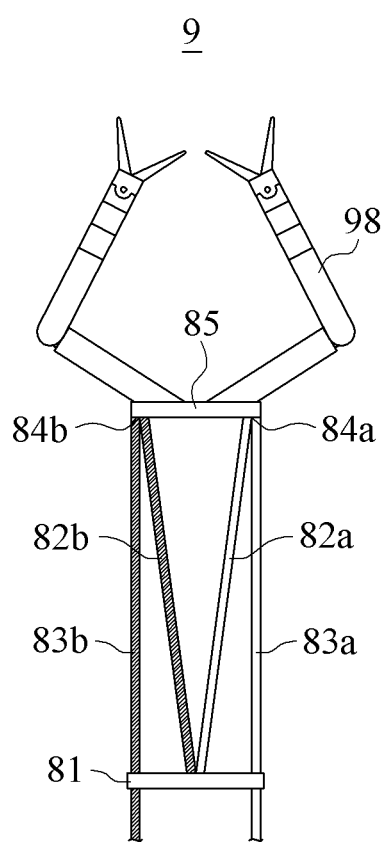
FIGS. 17A through 17C illustrate a robot arm according to at least one example embodiment.
Figure 17B:
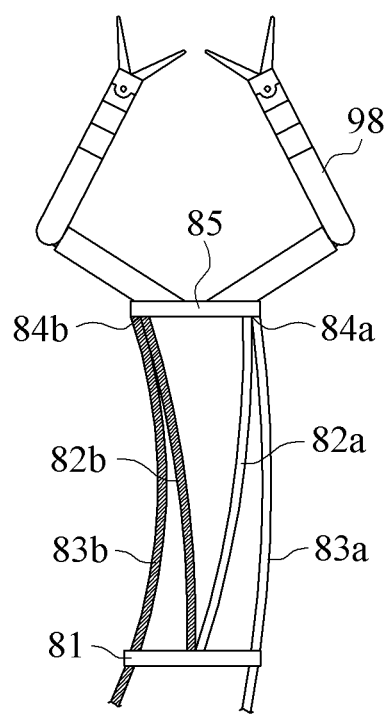
Figure 17C:
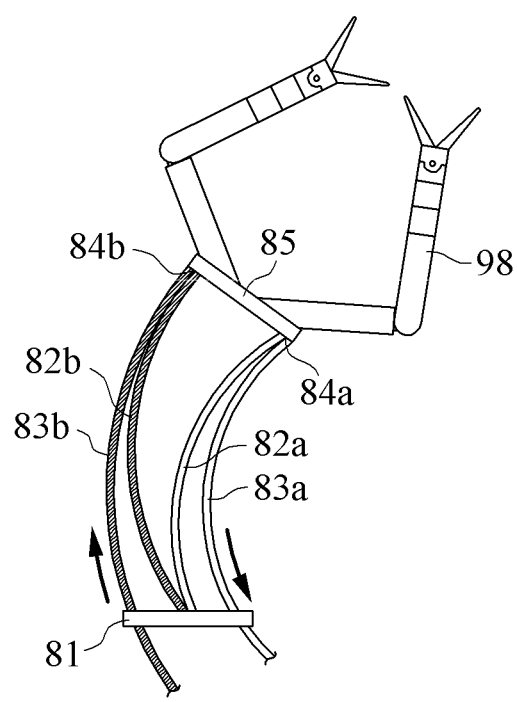

FIG. 17A illustrates a robot arm according to at least one example embodiment. FIG. 17B illustrates the robot arm to which a force is applied in a lateral direction according to at least one example embodiment. FIG. 17C illustrates an operation of the robot arm according to at least one example embodiment.

Referring to FIGS. 17A through 17C, a robot arm 9 may include the force transmitting frame 8 and an operator 98.

The force transmitting frame 8 may include the base 81, the first longitudinal member 82*a*, the second longitudinal member 83*a*, the third longitudinal member 82*b*, the fourth longitudinal member 83b, the first fastener 84a, the second fastener 84b, and the fastening member 85. The fastening member 85 may include a portion to be in direct contact with an object, for example, surgical equipment.

A middle region of the force transmitting frame 8 may be flexible. Thus, as shown in FIG. 17B, although a force is applied to the second longitudinal member 83a or the fourth longitudinal member 83b in a lateral direction, a relative angle of the fastening member 85 with respect to the base 81 may be maintained. Accordingly, when a force is applied to the force transmitting frame 8 in a lateral direction, an angle of the operator 98 connected to the fastening member 85 may be maintained.

Meanwhile, in a case in which the angle of the operator 98 needs to be changed, by sliding the second longitudinal member 83a and/or the fourth longitudinal member 83b with respect to the base 81, an angle or a position of the fastening member 85 may be changed.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A force transmitting frame configured to support a foot of a user, comprising:
   a base;
   a first longitudinal member connected to the base, the first longitudinal member having a first terminal end and a second terminal end in a length direction thereof;
   a second longitudinal member between the first longitudinal member and a ground when the user stands erect on the ground, the second longitudinal member configured to slide with respect to the base, the second longitudinal member having a first terminal end and a second terminal end in a length direction thereof; and
   a first fastener configured to fasten the first terminal end of the first longitudinal member directly to the first terminal end of the second longitudinal member.

2. The force transmitting frame of claim 1, wherein a middle region of the first longitudinal member and a middle region of the second longitudinal member are configured to move relative to each other.

3. The force transmitting frame of claim 1, wherein a middle region of each of the first longitudinal member and the second longitudinal member is flexible with respect to a force applied in a direction perpendicular to a longitudinal direction thereof.

4. The force transmitting frame of claim 1, wherein the force transmitting frame is shaped such that a distance between the first longitudinal member and the second longitudinal member increases from the first fastener toward the base.

5. The force transmitting frame of claim 1, wherein the force transmitting frame is shaped such that a distance between the first longitudinal member to the second longitudinal member is based on:

$$h(x) = \frac{F(L-x)}{T - F\sin\left(\operatorname{atan}\left(\frac{d}{dx}p(x)\right)\right)},$$

wherein h(x) denotes the distance between the first longitudinal member and the second longitudinal member, F denotes a magnitude of a force applied to the first fastener, T denotes a magnitude of a tensile force applied to the first longitudinal member, L denotes a length of the force transmitting frame from the first fastener to the base, x denotes a distance from the base of the force transmitting frame to a predetermined point of the second longitudinal member as the second longitudinal member slides through the base, and p(x) denotes a height of the first longitudinal member at a position the distance x away from the base.

6. The force transmitting frame of claim 1, further comprising:
   at least one distance maintaining member between the first longitudinal member and the second longitudinal member, the at least one distance maintaining member configured to maintain a distance between the first longitudinal member and the second longitudinal member.

7. The force transmitting frame of claim 6, wherein a height of the at least one distance maintaining member increases in a direction away from the first fastener.

8. The force transmitting frame of claim 1, further comprising:
   a third longitudinal member connected to the base;
   a fourth longitudinal member configured to slide with respect to the base;
   a second fastener configured to fasten a first end of the third longitudinal member to a first end of the fourth longitudinal member; and
   a fastening member configured to connect the first fastener and the second fastener.

9. The force transmitting frame of claim 8, wherein
   the second longitudinal member and the third longitudinal member are on opposite sides of the first longitudinal member, and
   the fourth longitudinal member and the first longitudinal member are on opposite sides of the third longitudinal member.

10. The force transmitting frame of claim 1, wherein
    the foot of the user including a rearfoot, a midfoot and a forefoot,
    the base is configured to support at least a portion of the rearfoot of the user,
    the first longitudinal member is configured to support at least a portion of the midfoot of the user, and
    the first fastener is configured to support at least a portion of the forefoot of the user.

11. A motion assistance apparatus, comprising:
    a supporting frame configured to support a first portion of a user;
    a joint assembly configured to assist a motion of a joint of the user; and
    a force transmitting frame configured to transmit a force to a foot of the user, the force transmitting frame including,
      a base connected to the joint assembly,
      a first longitudinal member connected to the base, the first longitudinal member having a first terminal end and a second terminal end in a length direction thereof,
      a second longitudinal member between the first longitudinal member and a ground when the user stands erect on the ground, the second longitudinal member configured to slide with respect to the base, the second longitudinal member having a first terminal end and a second terminal end in a length direction thereof, and a fastener configured to fasten the first terminal end of the first longitudinal member directly to the first terminal end of the second longitudinal member.

12. The motion assistance apparatus of claim 11, wherein the force transmitting frame further comprises:

at least one distance maintaining member between the first longitudinal member and the second longitudinal member, the at least one distance maintaining member configured to maintain a distance between the first longitudinal member and the second longitudinal member.

13. The motion assistance apparatus of claim 11, further comprising:

an actuator configured to transmit a power to the second longitudinal member; and a power transmitting cable configured to connect the actuator and the force transmitting frame.

14. The motion assistance apparatus of claim 13, wherein the actuator comprises:

an elastic body configured to provide an elastic force to the second longitudinal member; and an elastic body support connected to the joint assembly, the elastic body support configured to support the elastic body.

15. The motion assistance apparatus of claim 14, wherein the actuator further comprises:

a slider configured to slide with respect to the elastic body support, wherein the power transmitting cable is configured to connect the slider and the second longitudinal member, and the elastic body is between the elastic body support and the slider.

16. The motion assistance apparatus of claim 13, wherein the actuator comprises:

a driving source; and a rotary body connected to the driving source, the rotary body configured to wind and unwind the power transmitting cable.

17. The motion assistance apparatus of claim 13, further comprising:

a reducer between the actuator and the second longitudinal member, the reducer configured to increase the power transmitted from the actuator to the second longitudinal member.

18. The motion assistance apparatus of claim 17, wherein the reducer comprises:

a first movable pulley connected to the second longitudinal member, and wherein the power transmitting cable includes a first end portion, a second end portion and a middle portion therebetween, the first end portion being connected to the base, the second end portion is connected to the actuator, and the middle portion being wound around the first movable pulley.

19. The motion assistance apparatus of claim 11, wherein the force transmitting frame further comprises:

a third longitudinal member parallel to the second longitudinal member, and wherein the first longitudinal member includes a first branch and a second branch, the first branch having one end fastened to the second longitudinal member and the second branch having one end fastened to the third longitudinal member.

20. The motion assistance apparatus of claim 19, further comprising:

an actuator configured to transmit a power to the second longitudinal member and the third longitudinal member; and a reducer configured to increase the power, and to transmit the increased power to each of the second longitudinal member and the third longitudinal member.

21. The motion assistance apparatus of claim 20, wherein the reducer comprises:

a fixed pulley connected to the base;

a first movable pulley connected to the second longitudinal member;

a second movable pulley connected to the third longitudinal member;

a first power transmitter including a first end portion, a second end portion and a middle portion therebetween, the first end portion of the first power transmitter being connected to the actuator, the second end portion of the first power transmitter being connected to the base, and the middle portion of the first power transmitter being wound sequentially around the first movable pulley, the fixed pulley, and the second movable pulley; and a second power transmitter including a first end portion, a second end portion and a middle portion therebetween, the first end portion of the second power transmitter being connected to the actuator, the second end portion of the second power transmitter being connected to the base, and the middle portion of the second power transmitter being wound sequentially around the second movable pulley, the fixed pulley, and the first movable pulley.

22. A motion assistance apparatus comprising:

a supporting frame configured to support a first portion of a user;

a joint assembly configured to assist a motion of a joint of the user;

a force transmitting frame configured to transmit a force to a foot of the user, the force transmitting frame including, a base connected to the joint assembly, a first longitudinal member connected to the base, a second longitudinal member between the first longitudinal member and a ground when the user stands erect on the ground, the second longitudinal member configured to slide with respect to the base, and a fastener configured to fasten a first terminal end of the first longitudinal member directly to a first terminal end of the second longitudinal member;

an actuator configured to transmit a power to the second longitudinal member; and a power transmitting cable configured to connect the actuator and the force transmitting frame.

* * * * *